United States Patent [19]
Ramer et al.

[11] Patent Number: 6,001,962
[45] Date of Patent: Dec. 14, 1999

[54] MODIFIED FAS LIGANDS

[75] Inventors: J. Kevin Ramer, San Francisco; Lewis T. Williams, Tiburon, both of Calif.

[73] Assignee: The Regents of the University of California, Oakland, Calif.

[21] Appl. No.: 08/751,512

[22] Filed: Nov. 15, 1996

[51] Int. Cl.$^6$ .......................... A61K 38/00; A61K 39/00; C07K 1/00; C07H 21/04
[52] U.S. Cl. .......................... 530/324; 530/350; 530/351; 514/12; 424/185.1; 536/23.4
[58] Field of Search .................................. 536/23.1, 23.4; 424/185.1; 514/2, 12; 530/324, 350, 351

[56] References Cited

U.S. PATENT DOCUMENTS 5,731,425   3/1998   Brizzard et al. ....................... 536/23.1

FOREIGN PATENT DOCUMENTS

0675200A1   10/1995   European Pat. Off. .
96/40864    12/1996   WIPO .............................. C12N 1/21

OTHER PUBLICATIONS

Pitti et al, "Induction of apoptosis by Apo–2 ligand, a new member of the tumor necrosis factor cytokine family" J. Biol. Chem. vol. 271, No. 22, pp. 12687–12690, May 31, 1996.

Hollenbaugh, D. et al., "The human T cell antigen gp39, a member of the TNF gene family, is a ligand for the CD40 receptor: expression of a soluble form of gp39 with B cell co–stimulatory activity," *Embo J.* 11 (12) :4313–4321 (1992).

Korsmeyer, S.J., "Bcl–2 Initiates a New Category of Oncogenes: Regulators of Cell Death," *Blood* 80(4) :879–886 (1992).

Nagata, S. et al., "The Fas Death Factor," *Science* 267:1449–1455 (1995).

Ogasawara, J. et al., "Lethal effect of the anti–FAS antibody in mice," *Nature* 364:806–809 (1993).

Takahashi, T. et al., "Generalized Lymphoproliferative Disease in Mice, Caused by a Point Mutation in the Fas Ligand," *Cell* 76:969–976 (1994).

Tanaka, M. et al., "Expression of the functional soluble form of human Fas ligand in activated lymphocytes," *Embo J.* 14(6) :1129–1135 (1995).

Tanaka, M. et al., "Fas ligand in human serum," *Nature Medicine* 2(3) :317–322 (1996).

Watanabe–Fukunaga, R. et al., "Lymphoproliferation disorder in mice explained by defects in Fas antigen that mediates apoptosis," *Nature* 356:314–317 (1992).

Arnold. F. H. "Metal–affinity separations: a new dimension in protein processing" Bio/Technology. vol. 9. pp. 151–156, 1991.

*Primary Examiner*—Yvonne Eyler
*Attorney, Agent, or Firm*—Townsend and Townsend and Crew LLP

[57] ABSTRACT

The present invention generally provides modified polypeptides which are capable of interacting with the Fas receptor, nucleic acids encoding such polypeptides, cell lines capable of expressing these nucleic acids and secreting the polypeptides, and antibodies that are specifically immunoreactive with these polypeptides. The compositions of the present invention are generally useful for elucidating and modeling aspects of Fas biochemistry in vitro and manipulating Fas biology in vivo.

8 Claims, 5 Drawing Sheets

CD8 SIGNAL SEQUENCE ⟶

```
              10                  20                  30                  40
         *         *         *         *         *         *         *         *
ATG GCC TTA CCA GTG ACC GCC TTG CTC CTG CCG CTG GCC TTG
TAC CGG AAT GGT CAC TGG CGG AAC GAG GAC GGC GAC CGG AAC
 M   A   L   P   V   T   A   L   L   L   P   L   A   L
```

⟶ MATURE CD8 ⟶

```
              50                  60                  70                  80
         *         *         *         *         *         *         *         *
CTG CTC CAC GCC GCC AGG CCG│AGC CAG TTC CGG GTG TCG CCG
GAC GAG GTG CGG CGG TCC GGC│TCG GTC AAG GCC CAC AGC GGC
 L   L   H   A   A   R   P │ S   Q   F   R   V   S   P
```

```
              90                 100                 110                 120
         *         *         *         *         *         *         *         *         *
CTG GAT CGG ACC TGG AAC CTG GGC GAG ACA GTG GAG CTG AAG
GAC CTA GCC TGG ACC TTG GAC CCG CTC TGT CAC CTC GAC TTC
 L   D   R   T   W   N   L   G   E   T   V   E   L   K
```

```
             130                 140                 150                 160
         *         *         *         *         *         *         *         *
TGC CAG GTG CTG CTG TCC AAC CCG ACG TCG GGC TGC TCG TGG
ACG GTC CAC GAC GAC AGG TTG GGC TGC AGC CCG ACG AGC ACC
 C   Q   V   L   L   S   N   P   T   S   G   C   S   W
```

```
             170                 180                 190                 200                 210
         *         *         *         *         *         *         *         *         *
CTC TTC CAG CCG CGC GGC GCC GCC GCC AGT CCC ACC TTC CTC
GAG AAG GTC GGC GCG CCG CGG CGG CGG TCA GGG TGG AAG GAG
 L   F   Q   P   R   G   A   A   A   S   P   T   F   L
```

```
             220                 230                 240                 250
         *         *         *         *         *         *         *         *
CTA TAC CTC TCC CAA AAC AAG CCC AAG GCG GCC GAG GGG CTG
GAT ATG GAG AGG GTT TTG TTC GGG TTC CGC CGG CTC CCC GAC
 L   Y   L   S   Q   N   K   P   K   A   A   E   G   L
```

```
             260                 270                 280                 290
         *         *         *         *         *         *         *         *
GAC ACC CAG CGG TTC TCG GGC AAG AGG TTG GGG GAC ACC TTC
CTG TGG GTC GCC AAG AGC CCG TTC TCC AAC CCC CTG TGG AAG
 D   T   Q   R   F   S   G   K   R   L   G   D   T   F
```

FIG. 1A.

```
      300              310              320              330
 *     *     *     *     *     *     *     *     *
GTC   CTC   ACC   CTG   AGC   GAC   TTC   CGC   CGA   GAG   AAC   GAG   GGC   TAC
CAG   GAG   TGG   GAC   TCG   CTG   AAG   GCG   GCT   CTC   TTG   CTC   CCG   ATG
 V     L     T     L     S     D     F     R     R     E     N     E     G     Y 340              350              360              370
    *     *     *     *     *     *     *     *     *
TAT   TTC   TGC   TCG   GCC   CTG   AGC   AAC   TCC   ATC   ATG   TAC   TTC   AGC
ATA   AAG   ACG   AGC   CGG   GAC   TCG   TTG   AGG   TAG   TAC   ATG   AAG   TCG
 Y     F     C     S     A     L     S     N     S     I     M     Y     F     S 380              390              400              410              420
 *     *     *     *     *     *     *     *     *     *
CAC   TTC   GTG   CCG   GTC   TTC   CTG   CCA   GCG   AAG   CCC   ACC   ACG   ACG
GTG   AAG   CAC   GGC   CAG   AAG   GAC   GGT   CGC   TTC   GGG   TGG   TGC   TGC
 H     F     V     P     V     F     L     P     A     K     P     T     T     T 430              440              450              460
    *     *     *     *     *     *     *     *
CCA   GCG   CCG   CGA   CCA   CCA   ACA   CCG   GCG   CCC   ACC   ATC   GCG   TCG
GGT   CGC   GGC   GCT   GGT   GGT   TGT   GGC   CGC   GGG   TGG   TAG   CGC   AGC
 P     A     P     R     P     P     T     P     A     P     T     I     A     S 470              480              490              500
    *     *     *     *     *     *     *     *
CAG   CCC   CTG   TCC   CTG   CGC   CCA   GAG   GCG   TGC   CGG   CCA   GCG   GCG
GTC   GGG   GAC   AGG   GAC   GCG   GGT   CTC   CGC   ACG   GCC   GGT   CGC   CGC
 Q     P     L     S     L     R     P     E     A     C     R     P     A     A

CD8 ─────────▶│XhoI
      510              520              530              540
 *     *     *     *     *     *     *     *     *
GGG   GGC   GCA   GTG   CAC   ACG   AGG   GGG   CTG   GAC   TTC   GCC   TGT│  CTC
CCC   CCG   CGT   CAC   GTG   TGC   TCC   CCC   GAC   CTG   AAG   CGG   ACA│  GAG
 G     G     A     V     H     T     R     G     L     D     F     A     C │   L

│            HEXAHISTIDINE                │ EcoRI │◀─── Glu-Glu EPITOPE
   550                   560                  │  570  │       580
    │ *     *     *     *     *     *    *    │ *     │ *     *     *     *
GAG │CAT   CAC   CAT   CAC   CAT   CAC       │GAA   TTC│GAA   TAC   ATG   CCA   ATG
CTC │GTA   GTG   GTA   GTG   GTA   GTG       │CTT   AAG│CTT   ATG   TAC   GGT   TAC
 E  │ H     H     H     H     H     H         │ E     F │ E     Y     M     P     M
```

FIG. 1B.

```
      FasL
590           600           610           620           630
 *     *       *      *      *      *      *      *      *
GAA│CAG  CTC  TTC  CAC  CTA  CAG  AAG  GAG  CTG  GCA  GAA  CTC  CGA
CTT│GTC  GAG  AAG  GTG  GAT  GTC  TTC  CTC  GAC  CGT  CTT  GAG  GCT
 E │ Q    L    F    H    L    Q    K    E    L    A    E    L    R 640           650           660           670
  *     *     *      *      *      *      *      *
GAG  TCT  ACC  AGC  CAG  ATG  CAC  ACA  GCA  TCA  TCT  TTG  GAG  AAG
CTC  AGA  TGG  TCG  GTC  TAC  GTG  TGT  CGT  AGT  AGA  AAC  CTC  TTC
 E    S    T    S    Q    M    H    T    A    S    S    L    E    K 680           690           700           710
  *     *     *      *      *      *      *      *
CAA  ATA  GGC  CAC  CCC  AGT  CCA  CCC  CCT  GAA  AAA  AAG  GAG  CTG
GTT  TAT  CCG  GTG  GGG  TCA  GGT  GGG  GGA  CTT  TTT  TTC  CTC  GAC
 Q    I    G    H    P    S    P    P    P    E    K    K    E    L 720           730           740           750
  *     *      *      *      *      *      *      *      *
AGG  AAA  GTG  GCC  CAT  TTA  ACA  GGC  AAG  TCC  AAC  TCA  AGG  TCC
TCC  TTT  CAC  CGG  GTA  AAT  TGT  CCG  TTC  AGG  TTG  AGT  TCC  AGG
 R    K    V    A    H    L    T    G    K    S    N    S    R    S 760           770           780           790
  *     *      *      *      *      *      *      *
ATG  CCT  CTG  GAA  TGG  GAA  GAC  ACC  TAT  GGA  ATT  GTC  CTG  CTT
TAC  GGA  GAC  CTT  ACC  CTT  CTG  TGG  ATA  CCT  TAA  CAG  GAC  GAA
 M    P    L    E    W    E    D    T    Y    G    I    V    L    L 800           810           820           830           840
 *     *      *      *      *      *      *      *      *
TCT  GGA  GTG  AAG  TAT  AAG  AAG  GGT  GGC  CTT  GTG  ATC  AAT  GAA
AGA  CCT  CAC  TTC  ATA  TTC  TTC  CCA  CCG  GAA  CAC  TAG  TTA  CTT
 S    G    V    K    Y    K    K    G    G    L    V    I    N    E 850           860           870           880
       *      *      *      *      *      *      *      *
ACT  GGG  CTG  TAC  TTT  GTA  TAT  TCC  AAA  GTA  TAC  TTC  CGG  GGT
TGA  CCC  GAC  ATG  AAA  CAT  ATA  AGG  TTT  CAT  ATG  AAG  GCC  CCA
 T    G    L    Y    F    V    Y    S    K    V    Y    F    R    G
```

FIG. 1C.

```
          890             900             910             920
   *       *       *       *       *       *       *       *
  CAA TCT TGC AAC AAC CTG CCC CTG AGC CAC AAG GTC TAC ATG
  GTT AGA ACG TTG TTG GAC GGG GAC TCG GTG TTC CAG ATG TAC
   Q   S   C   N   N   L   P   L   S   H   K   V   Y   M 930             940             950             960
   *       *       *       *       *       *       *       *       *
  AGG AAC TCT AAG TAT CCC CAG GAT CTG GTG ATG ATG GAG GGG
  TCC TTG AGA TTC ATA GGG GTC CTA GAC CAC TAC TAC CTC CCC
   R   N   S   K   Y   P   Q   D   L   V   M   M   E   G 970             980             990            1000
   *       *       *       *       *       *       *       *
  AAG ATG ATG AGC TAC TGC ACT ACT GGG CAG ATG TGG GCC CGC
  TTC TAC TAC TCG ATG ACG TGA TGA CCC GTC TAC ACC CGG GCG
   K   M   M   S   Y   C   T   T   G   Q   M   W   A   R 1010         1020             1030            1040         1050
   *    *       *       *       *       *       *       *    *
  AGC AGC TAC CTG GGG GCA GTG TTC AAT CTT ACC AGT GCT GAT
  TCG TCG ATG GAC CCC CGT CAC AAG TTA GAA TGG TCA CGA CTA
   S   S   Y   L   G   A   V   F   N   L   T   S   A   D 1060            1070            1080            1090
   *       *       *       *       *       *       *       *
  CAT TTA TAT GTC AAC GTA TCT GAG CTC TCT CTG GTC AAT TTT
  GTA AAT ATA CAG TTG CAT AGA CTC GAG AGA GAC CAG TTA AAA
   H   L   Y   V   N   V   S   E   L   S   L   V   N   F 1100            1110            1120            1130
   *       *       *       *       *       *       *       *
  GAG GAA TCT CAG ACG TTT TTC GGC TTA TAT AAG CTC TAA
  CTC CTT AGA GTC TGC AAA AAG CCG AAT ATA TTC GAG ATT
   E   E   S   Q   T   F   F   G   L   Y   K   L   *
```

*FIG. 1D.*

MODIFIED FAS LIGANDS

BACKGROUND OF THE INVENTION

Apoptosis, or programmed cell death, is an important physiological process in multicellular organisms, both during development and for homeostasis. Apoptosis permits the elimination of cells that are no longer necessary, that are produced in excess, that have developed improperly, or that have sustained genetic damage. Apoptosis occurs in many different tissue systems and must be properly regulated to maximize the benefit to the individual. Conversely, dysregulation of the apoptotic mechanism can result in the development of significant disease which results from either inhibition of and/or inappropriate cell death. For example, inhibition of cell death may contribute to disease in the immune system by allowing persistence of self-reactive B and T cells, thereby promoting autoimmune disorders. See, e.g., Watanabe-Fukunaga et al., Nature 356:314–317 (1992). Additionally, inhibition or failure of the cell death mechanism may permit such cells to undergo mutations leading to a transformed or cancerous state. See, e.g., Korsmeyer, Blood 80:879–886 (1992).

Apoptosis is mediated, at least in part, by a cell surface receptor protein, Fas, which plays an important role in the development and function of the immune system. Malfunction of the Fas system has been shown to cause lymphoproliferative disorders and accelerate autoimmune disorders. Takahashi et al., Cell 76:969–976 (1994). Further, exacerbation of Fas-mediated apoptosis has been implicated as leading to excessive tissue destruction. Ogasawara et al., Nature 364:806–809 (1993).

The Fas ligand (FasL) binds to and activates the Fas receptor to initiate the apoptotic mechanism. For an overview of Fas receptor mediated apoptosis, see, e.g, Nagata et al., Science 267:1449–1455 (1995). In normal physiological contexts, FasL exists predominantly as a type II membrane protein. Supraphysiological states, e.g., in vitro overexpression, or pathophysiological states, e.g., specific leukemias or lymphomas, exhibit some release of a proteolytically processed form of FasL. See, e.g., Tanaka et al., Nature Medicine 2:317–322 (1996). Additionally, production of a soluble form of FasL may occur upon activation of lymphocytes. Tanaka et al., EMBO J. 14:1129–1135 (1995). However, the prevalence of soluble FasL in vivo is not known.

It would generally be desirable to be able to produce a soluble compound that functions as the naturally occurring Fas ligand in its interactions with the Fas receptor, i.e., receptor binding and/or activation of receptor mediated pathways, for use in modeling this interaction as well as providing an external method of regulating this interaction. The present invention meets these and other needs.

SUMMARY OF THE INVENTION

The present invention generally provides soluble polypeptides that are capable of specifically interacting with the Fas receptor, either to simulate the activity of naturally occuring FasL, i.e., to activate Fas receptor mediated pathways, also termed "Fas mediated" pathways, methods and compositions for producing these polypeptides, and methods for using these polypeptides in screening, therapeutic and other applications.

It is therefore an aspect of the present invention to provide substantially pure soluble polypeptides that are capable of specifically interacting with a Fas receptor. These polypeptides will generally comprise an extracellular portion of the Fas ligand, FasL, but generally lack the transmembrane portion of FasL. These polypeptides may generally be used in a variety of applications including as in vitro and in vivo models to screen for compounds that are capable of affecting the Fas receptor/FasL interaction, either as enhancers or inhibitors.

For example, in one aspect, these polypeptides may be used in methods of detecting the presence or absence of a Fas receptor in a mixture of proteins. These methods typically comprise immobilizing the mixture of proteins on a solid support, followed by contacting the immobilized proteins with a polypeptide of the invention, which polypeptide also comprises a detectable label. The immobilized mixture is then washed to remove unbound proteins. One then determines the presence or absence of Fas receptor in the mixture by determining the presence or absence of the detectable label bound to the solid support, e.g., complexed to bound Fas receptor.

In a similar method, the polypeptides described herein are used in methods of purifying Fas receptors from a mixture of proteins. Here, the polypeptide, which is capable of binding to the Fas receptor, is provided immobilized on the solid support. The mixture of proteins is contacted with the solid support, then washed to remove unbound proteins. Substantially pure Fas receptor is then eluted from the solid support.

In a further aspect, these polypeptides may be used in therapeutic applications. For example another aspect of the invention provides a method of treating a patient for a disorder characterized by inadequate stimulation or under-stimulation of a Fas receptor-mediated pathway. The method comprises administering to the patient a pharmaceutical composition which comprises an effective amount of a polypeptide of the invention capable of specifically activating a Fas receptor mediated pathway.

In another aspect, the present invention provides isolated nucleic acid sequences, said nucleic acid sequence encodes the polypeptides of the invention. These nucleic acids may generally be used in the production of recombinant cell lines that are capable of secreting the polypeptides of the present invention.

The present invention also provides isolated antibodies that are capable of specifically recognizing the polypeptides of the present invention.

BRIEF DESCRIPTION OF THE DRAWINGS

FIG. 1A–1C (SEQ ID NOS:7–8) show the nucleotide sequence (SEQ ID NO:7) and amino acid sequence (SEQ ID NO:8) of the modified Fas ligand secFL. The CD8 secretion sequence, glu-glu epitope tag, hexahistidine motif and FasL extracellular portion are indicated.

DESCRIPTION OF THE PREFERRED EMBODIMENT

I. General

Figure 2:
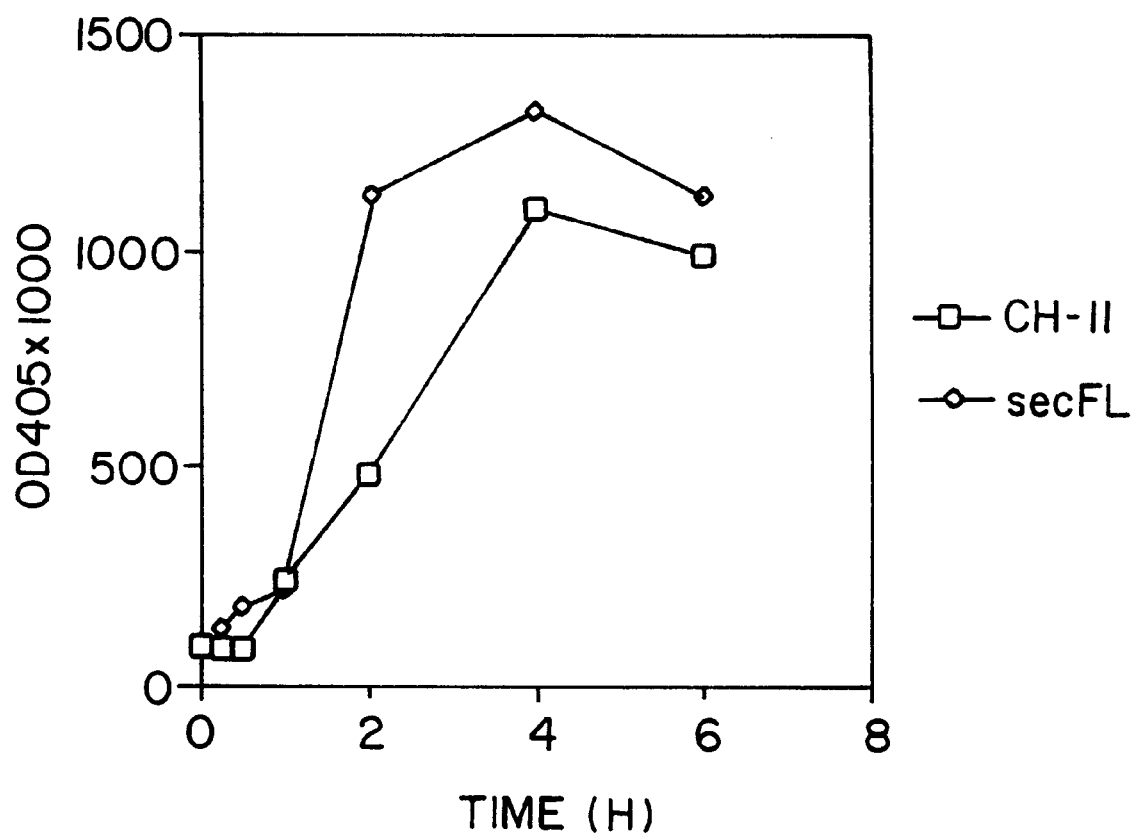
FIG. 2 shows a graphical comparison of cell death for Jurkat T cells treated with CH11 anti-Fas IgM (positive control, —□—) and secFL (—♦—). Cell death was measured by DNA fragmentation.

The present invention generally provides novel soluble polypeptides which are capable of interacting with the Fas receptor, nucleic acids encoding such polypeptides, cell lines capable of expressing these nucleic acids and secreting the polypeptides, and antibodies that are specifically immunoreactive with these polypeptides. The compositions of the present invention are generally useful for elucidating and modeling aspects of Fas biochemistry in vitro and manipulating Fas biology in vivo.

II. Poly-petides, Analogs, Mimics

As noted above, in a first aspect, the present invention provides substantially pure or isolated soluble polypeptides that are capable of specifically interacting with the Fas receptor. The terms "substantially pure" or "isolated", when referring to proteins and polypeptides, denote those polypeptides that are generally separated from proteins or other contaminants with which they are typically associated. A protein or polypeptide is considered substantially pure when that polypeptide makes up greater than about 50% of the total protein content of the composition containing that polypeptide, and typically, greater than about 60% of the total protein content. More typically, a substantially pure or isolated protein or polypeptide will make up from about 75 to about 90% of the total protein. Preferably, the polypeptide will make up greater than about 90%, and more preferably, greater than about 95% of the total protein in the composition.

By "capable of specifically interacting with the Fas receptor" is meant that the subject polypeptides are capable of at least one of a broad range of specific interactions with the Fas receptor. Included in these specific interactions are the ability to activate the Fas receptor or initiate Fas receptor mediated signalling pathways, specific binding to the Fas receptor, both with and without activation, and the like.

By way of example, in one aspect, the polypeptides may be characterized by their ability to affect Fas receptor mediated pathways or signal cascades. In particular, the polypeptides of the invention may be characterized by their ability to activate Fas receptor mediated pathways, e.g., apoptosis. By "activate Fas receptor mediated pathways" is meant the initiation of a signalling event or cascade within a biological system which is normally initiated by the binding of a ligand to the Fas receptor (i.e., in vivo). The signal cascade then leads to a catabolic or anabolic reaction within a biological system, e.g., cells. In particularly preferred aspects, the Fas receptor mediated pathway is apoptosis, and the catabolic reaction is cell death. Activation of Fas-mediated apoptosis may generally be determined by known cell death or cell viability assays, such as DNA fragmentation ELISAs or viability staining using, e.g., WST-1 staining.

Polypeptides of the present invention may also be used to accomplish the converse of those goals described above. Specifically, in an alternative aspect, polypeptides according to the present invention may be used to inhibit or otherwise block the interaction between the Fas receptor and its naturally occurring ligands, e.g., FasL. Consequently, these polypeptides may be used to block activation of Fas receptor mediated pathways. In order to provide blocking activity, the polypeptides of the present invention will generally include only that portion of the FasL extracellular region necessary for binding the Fas receptor, without activation of the Fas receptor. Binding of the resulting ligand fragment to the receptor sterically interferes with interaction of the receptor and its natural ligand, i.e., endogenous FasL. Identification of specific fragments of the FasL extracellular region that are capable of this blocking activity may generally be carried out by a variety of methods, including, e.g., deletion mutagenesis, or chemical or enzymatic cleavage of full length FasL, and the like, followed by assaying the resulting fragments using the assay methods described above.

In addition to their ability to specifically interact with the Fas receptor, the polypeptides of the present invention are also characterized by their structure. Specifically, these polypeptides comprise an extracellular portion of FasL, but lack a transmembrane region. Deletion of the transmembrane region provides at least a two-part benefit. First, the resulting polypeptides are generally soluble in low ionic strength aqueous solutions (e.g., greater than 90% soluble in aqueous solutions), and second, the polypeptides may be recombinantly produced in secreted form. This latter benefit permits production of large amounts of the subject polypeptides for use in the various applications described herein.

In preferred aspects, the polypeptides of the invention will also include a heterologous marker sequence. By "heterologous marker sequence" is meant a sequence of amino acids contained within or at one or the other terminus of the overall sequence of the subject polypeptide, which marker sequence is non-native to the FasL sequence, and which is capable of specific detection or binding through the use of an external agent, e.g., an affinity tag such as an antibody, ligand, etc. Particularly preferred marker sequences include antibody epitopes such as, the glu-glu epitope tag, FLAG epitope, influenza virus hemagglutinin (IHA) epitope tag, or glutathione-S-transferase, or a hexahistidine motif that is bound by metal affinity resin. Typically, the hexahistidine motif is particularly preferred for its ability to function as an affinity purification target under relatively mild purification protocols.

In additional preferred aspects, the polypeptides of the present invention will include a secretion direction sequence, in addition to the extracellular portion of the FasL. By "secretion direction sequence" is meant a sequence of amino acids which functions to direct the secretion of the polypeptide from a cell synthesizing the polypeptide. Examples of such secretion direction sequences, as well as their use in fusion proteins to direct the secretion of heterologous polypeptides are well known in the art, and include, e.g. the CD8 signal sequence (Hollenbaugh et al., EMBO J. 11:4313–4321 (1992)), the signal sequence from the baculoviral GP67 protein (available from Pharmingen, Inc.), signal sequence from granulocyte colony-stimulating factor (Tanaka et al., EMBO J. 14:1129–1135), and the like.

In particularly preferred aspects, the polypeptides of the present invention may generally be characterized by their structural relation to the secreted modified FasL polypeptide sequence (also termed "secFL") shown in FIGS. 1A–1C (SEQ ID NO:8) The secFl polypeptide shown in FIGS. 1A–1C (SEQ ID NO:8) includes the extracellular domain of FasL fused to the extracellular domain of CD8, linked via a hexahistidine motif and glu-glu epitope tag. In preferred aspects, the polypeptides will have an amino acid sequence that is substantially homologous to the amino acid sequence shown in FIGS. 1A–1C (SEQ ID NO:8), or biologically active fragments thereof. In still more preferred aspects, the polypeptides of the invention will have the amino acid sequence shown in FIGS. 1A–1C (SEQ ID NO:8), or conservative substitutions thereof.

The term "biologically active fragment" as used herein, refers to portions of the proteins or polypeptides, which portions possess one of the particular biological activities described above, e.g., the ability to specifically interact with the Fas receptor. With regard to the polypeptides of the present invention, particularly preferred polypeptides or biologically active fragments include, e.g., polypeptides that activate or initiate Fas receptor mediated pathways and/or are able to affect the interaction of the Fas receptor with a Fas ligand, e.g., to block or otherwise inhibit through binding to the Fas receptor. Fragments that are specifically recognized and bound by antibodies raised against the polypeptides of the invention are also included in the definition of biologically active fragments. Such fragments are also referred to herein as "immunologically active fragments."

Biologically active fragments of the polypeptides of the invention will generally be useful where use of a full length protein is unsuitable for the particular application. Such applications include modelling of analogs, mimics, or small molecules, or therapeutic applications where administration of larger polypeptides is impracticable.

Generally, biologically active fragments of the above described proteins may include any subsequence of a full length FasL polypeptide shown in FIGS. 1A–1C (SEQ ID NO:8). Typically, however, such fragments will be from about 5 to about 1000 amino acids in length. More typically, these peptides will be from about 10 to about 500 amino acids in length, more typically about 10 to about 250 amino acids in length, and preferably from about 20 to about 200 amino acids in length. Generally, the length of the fragment may depend, in part, upon the application for which the particular peptide is to be used. For example, for raising antibodies, the peptides may be of a shorter length, e.g., from about 5 to about 50 amino acids in length, whereas for binding or binding inhibition applications, the peptides will generally have a greater length, e.g., from about 10 to about 1000 amino acids in length, preferably, from about 20 to about 500 amino acids in length, and more preferably, from about 20 to about 200 amino acids in length.

Selection of biologically active fragments of the sequence shown in FIGS. 1A–1C (SEQ ID NO:8) may generally be carried out by the methods described herein. For example, selective proteolytic digestion, recombinant deletional methods or de novo peptide synthesis methods may be employed to identify portions of the above described polypeptides that possess the desired biological activity, e.g., Fas receptor binding, inhibition of Fas receptor/FasL interaction, activation of Fas mediated apoptosis. See, e.g., Sambrook et al., Molecular Cloning: A Laboratory Manual, (2nd ed.) Vols. 1–3, Cold Spring Harbor Laboratory, (1989). Once such fragments are generated, they are then assayed to determine if they possess the biological activity that is sought. For example, as described in greater detail in the context of the applications of these polypeptides, fragments may be screened for their ability to bind Fas receptor by blotting the fragment on a solid support, e.g., nitrocellulose, PVDP etc, and probing the fragment with labelled FasL, to identify fragments to which the Fas receptor binds. Alternatively, the fragments may be screened in a cell death assay, as described herein, to determine if the fragment possesses the capability to activate Fas receptor mediated cell death, or apoptosis.

Also included within the definition of "biologically active fragments," are those polypeptides or fragments of the invention which are characterized by their ability to bind antibodies raised against proteins or polypeptides having the amino acid sequence of secFL, as shown in FIGS. 1A–1C (SEQ ID NO:8), or fragments thereof. The antibodies generally recognize polypeptides that are substantially homologous to the secFL protein shown in FIGS. 1A–1C (SEQ ID NO:8), or fragments thereof. A variety of immunoassay formats may be used to select antibodies specifically immunoreactive with a particular protein or domain. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity. Antibodies specifically immunoreactive with the polypeptides of the present invention are discussed in greater detail, below.

The terms "substantially homologous" when referring to polypeptides, refer comparatively to two amino acid sequences which, when optimally aligned, are at least about 75% homologous, preferably at least about 85% homologous more preferably at least about 90% homologous, and still more preferably at least about 95% homologous. Optimal alignment of sequences for aligning a comparison window may be conducted by the local homology algorithm of Smith and Waterman (1981) Adv. Appl. Math. 2:482, by the homology alignment algorithm of Needleman and Wunsch (1970) J. Mol. Biol. 48:443, by the search for similarity method of Pearson and Lipman (1988) Proc. Natl. Acad. Sci. (USA) 85:2444, or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As alluded to above, the polypeptides of the present invention may generally be prepared using recombinant or synthetic methods that are well known in the art. Recombinant techniques are generally described in Sambrook, et al., Molecular Cloning: A Laboratory Manual, (2nd ed.) Vols. 1–3, Cold Spring Harbor Laboratory, (1989). Techniques for the synthesis of polypeptides are generally described in Merrifield, J. Amer. Chem. Soc. 85:2149–2456 (1963), Atherton, et al., Solid Phase Peptide Synthesis: A Practical Approach, IRL Press (1989), and Merrifield, Science 232:341–347 (1986). In preferred aspects, the polypeptides of the present invention may be expressed by a suitable host cell that has been transfected with a nucleic acid of the invention, as described in greater detail below.

Isolation and purification of the polypeptides of the present invention can also be carried out by methods that are generally well known in the art. For example, the polypeptides may be purified using readily available precipitation or chromatographic methods, e.g., ion exchange, hydrophobic interaction, HPLC or affinity chromatography, to achieve the desired purity. Affinity chromatography may be particularly attractive in allowing an individual to take advantage of the specific biological activity of the desired polypeptide, e.g., Fas receptor binding, presence of antigenic determinants or the like. For example, as noted above, preferred polypeptides also comprise a heterologous marker sequence which may be used to purify the subject polypeptides. For example, in the case of those polypeptides that comprise a hexahistidine motif, metal affinity resins may be used in their purification. Similarly, for other markers, i.e., the influenza hemagglutinin epitope tag or glu-glu epitope tag, polypeptides may be precipitated using monoclonal antibodies which specifically recognize these tags. Briefly, antibodies that recognize the marker sequence tags, or antibodies to the FasL extracellular region, may be coupled to a suitable solid support and contacted with a mixture of proteins containing the polypeptides of the invention under conditions conducive to the association of these polypeptides with the antibody. Once bound to the immobilized antibody, the solid support is washed to remove unbound material and/or nonspecifically bound proteins. The desired polypeptides may then be eluted from the solid support in substantially pure form by, e.g., a change in salt, pH or buffer concentration. Suitable solid supports for affinity purifications are well known in the art and are generally commercially available from, e.g., Pharmacia, Inc., or Sigma Chemical Co. Examples of such solid supports include agarose, cellulose, dextran, silica, polystyrene or other similar solid supports.

In addition to those polypeptides and fragments described above, the present invention also provides fusion proteins which contain these polypeptides or fragments. The term "fusion protein" as used herein, generally refers to a composite protein, i.e., a single contiguous amino acid sequence, made up of two distinct, heterologous polypeptides which are not normally fused together in a single amino acid sequence. Thus, a fusion protein may include a single amino acid sequence that contains two entirely distinct amino acid sequences or two similar or identical polypeptide sequences, provided that these sequences are not normally found together in a single amino acid sequence. Fusion proteins may generally be prepared using either recombinant nucleic acid methods, i.e., as a result of transcription and translation of a gene fusion, which fusion comprises a segment encoding a polypeptide of the invention and a segment encoding a heterologous protein, or by chemical synthesis methods well known in the art. In a particularly preferred aspect, the polypeptides of the invention are provided as a fusion protein, wherein the extracellular portion of FasL is fused to a heterologous amino acid sequence that promotes secretion of the polypeptides from cells producing those polypeptides. For example, FIGS. 1A–1C (SEQ ID NO:8) illustrates the FasL extracellular region fused to the extracellular domain of CD8. This sequence includes a short stretch of hydrophobic amino acids at the N-terminus which directs secretion of the polypeptide. This signal sequence is proteolytically cleaved during secretion of the peptide, leaving the mature CD8 extracellular domain fused to the soluble FasL extracellular portion. The mature CD8 extracellular domain provides an additional marker sequence, for its purification and/or detection. Additionally, as the nature of CD8 as a homodimeric protein results from sequences in the extracellular region of the protein, the inclusion of this sequence also promotes oligomerization of the FasL polypeptide.

Also included within the present invention are amino acid variants of the above described polypeptides. These variants may include insertions, deletions and substitutions with other amino acids. For example, in some aspects, conservative amino acid substitutions may be made, i.e., substitution of selected amino acids with different amino acids having similar structural characteristics, e.g., net charge, hydrophobicity and the like. Glycosylation modifications, either changed, increased amounts or decreased amounts, as well as other sequence modifications are also envisioned.

Systematic substitution of one or more amino acids of a consensus sequence with a D-amino acid of the same type (e.g., D-lysine in place of L-lysine) may also be used to generate more stable polypeptides. In addition, constrained polypeptides comprising a consensus sequence or a substantially identical consensus sequence variation may be generated by methods known in the art (Rizo and Gierasch (1992) Ann. Rev. Biochem. 61:387; for example, by adding internal cysteine residues capable of forming intramolecular disulfide bridges which cyclize the polypeptide. Similarly, modification of the amino or carboxy terminals may also be used to confer stabilizing properties upon the polypeptides of the invention, e.g., amidation of the carboxy-terminus or acylation of the amino-terminus. Substitution of amino acids involved in the activation of the Fas receptor, can be used to generate dominant negative inhibitors of FasL Fas receptor interactions.

Furthermore, although primarily described in terms of "proteins" or "polypeptides" one of skill in the art, upon reading the instant specification, will appreciate that these terms also include structural analogs and derivatives of the above-described polypeptides, e.g., polypeptides having conservative amino acid insertions, deletions or substitutions, peptidomimetics and the like. For example, in addition to the above described polypeptides which consist only of naturally-occurring amino acids, peptidomimetics of the polypeptides of the present invention are also provided. Peptide analogs are commonly used in the pharmaceutical industry as non-peptide drugs with properties analogous to those of the template peptide. These types of non-peptide compounds are termed "peptide mimetics" or "peptidomimetics" (Fauchere, J. (1986) Adv. Drug Res. 15:29; Veber and Freidinger (1985) TINS p.392; and Evans et al. (1987) J. Med. Chem 30:1229, and are usually developed with the aid of computerized molecular modeling. Peptide mimetics that are structurally similar to therapeutically useful peptides may be used to produce an equivalent therapeutic effect. Generally, peptidomimetics are structurally similar to a paradigm polypeptide (i.e., a polypeptide that has a biological or pharmacological activity), such as naturally-occurring receptor-binding polypeptide, but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art and further described in the following references: Spatola, A.F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., Trends Pharm Sci (1980) pp. 463–468 (general review); Hudson, D. et al., Int J Pept Prot Res (1979) 14:177–185 (—CH$_2$NH—, CH$_2$CH$_2$—); Spatola, A.F. et al., Life Sci (1986) 38:1243–1249 (—CH2—S); Hann, M. M., J. Chem Soc Perkin Trans I (1982) 307–314 (—CH—CH—, cis and trans); Almquist, R.G. et al., J Med Chem (1980) 23:1392–1398 (—COCH$_2$—); Jennings-White, C. et al., Tetrahedron Lett (1982) 23:2533 (—COCH$_2$—); Szelke, M. et al., European Appln. EP 45665 (1982) CA: 97:39405 (1982) (—CH(OH)CH$_2$—); Holladay, M. W. et al., Tetrahedron Lett (1983) 24:4401–4404 (—C(OH)CH$_2$—); and Hruby, V. J., Life Sci (1982) 31:189–199 (—CH$_2$—S—).

Peptide mimetics may have significant advantages over polypeptide embodiments, including, for example: more economical production; greater chemical stability; enhanced pharmacological properties (half-life, absorption, potency, efficacy, etc.); altered specificity (e.g., a broad-spectrum of biological activities); reduced antigenicity; and others.

For many applications, it may also be desirable to provide the polypeptides of the invention as labeled entities, i.e., covalently attached or linked to a detectable group, to facilitate identification, detection and quantification of the polypeptide in a given circumstance. These detectable groups may comprise a detectable protein group, e.g., an assayable enzyme or antibody epitope as described above in the discussion of fusion proteins. Alternatively, the detectable group may be selected from a variety of other detectable groups or labels, such as radiolabels (e.g., $^{125}$I, $^{32}$P or $^{35}$S) or a chemiluminescent or fluorescent group., Similarly, the detectable group may be a substrate, cofactor, inhibitor or affinity ligand. Labeling of peptidomimetics usually involves covalent attachment of one or more labels, directly or through a spacer (e.g., an amide group), to non-interfering positions) on the peptidomimetic that are predicted by quantitative structure-activity data and/or molecular modeling. Such non-interfering positions generally are positions that do not form direct contacts with the molecules to which the peptidomimetic binds (e.g., Fas receptor) to produce the therapeutic effect. Derivatization (e.g., labeling) of peptidomimetics should not substantially interfere with the desired biological or pharmacological activity of the peptidomimetic. Generally, peptidomimetics of peptides of the invention bind to the Fas receptor with high affinity and/or possess detectable biological activity (i.e., ability to enhance or inhibit one or more Fas receptor mediated phenotypic changes).

III. Nucleic acids

In another aspect, the present invention provides nucleic acids which encode the polypeptides of the invention, as well as expression vectors that include these nucleic acids, and cell lines and organisms that are capable of expressing these nucleic acids. These nucleic acids, expression vectors and cell lines may generally be used to produce the polypeptides of the invention. Generally, the isolated nucleic acids of the present invention encode a polypeptide which is capable of specifically interacting with the Fas receptor, and which comprises an extracellular portion of the FasL, but not the transmembrane region.

Typically, however, the nucleic acids of the invention encode a polypeptide that also includes a heterologous marker sequence. In preferred aspects, the nucleic acids of the present invention encode an amino acid sequence that is substantially homologous to the amino acid sequences shown in FIGS. 1A–1C (SEQ ID NO:7). More preferred are those isolated nucleic acid sequences that comprise a nucleotide sequence that is substantially homologous to the nucleotide sequences shown in FIGS. 1A–1C (SEQ ID NO:7).

"Nucleic acids" of the present invention include RNA, cDNA, genomic DNA, synthetic forms and mixed polymers, both sense and antisense strands. Furthermore, different alleles of each isoform are also included. The present invention also provides recombinant nucleic acids which are not otherwise naturally occurring. The nucleic acids described herein also include self replicating plasmids and infectious polymers of DNA or RNA. Unless specified otherwise, conventional notation for nucleic acids is used herein. For example, as written, the left hand end of a single stranded polynucleotide sequence is the 5'-end, whereas the right-hand end is the 340 -end. The left hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The nucleic acids of the present invention may be present in whole cells, cell lysates or in partially pure or substantially pure or isolated form. When referring to nucleic acids, the terms "substantially pure" or "isolated" generally refer to the nucleic acid separated from contaminants with which it is generally associated, e.g., lipids, proteins and other nucleic acids. The substantially pure or isolated nucleic acids of the present invention are generally greater than about 50% pure. Typically, these nucleic acids are more than about 60% pure, more typically, from about 75% to about 90% pure and preferably from about 95% to about 98% pure.

The DNA compositions generally include a coding region which encodes a polypeptide that is capable of specifically interacting with a Fas receptor. These nucleic acids, or fragments may comprise part or all of the cDNA sequence that encodes the polypeptides of the present invention. Preferred nucleic acids will typically encode polypeptides having a heterologous marker sequence and/or a secretion direction sequence, as described above. Even more preferred nucleic acids encode an amino acid sequence which is substantially homologous to the amino acid sequence shown in FIGS. 1A–1C (SEQ ID NO:8), or biologically active fragments thereof. More preferred nucleic acids comprise a segment having more than about 20 contiguous nucleotides from the nucleotide sequences shown in FIGS. 1A–1C (SEQ ID NO:7), with still more preferred nucleic acids having a nucleotide sequence that is substantially homologous to the sequence shown in FIGS. 1A–1C (SEQ ID NO:7).

The phrase "nucleic acid sequence encoding" refers to a nucleic acid which directs the expression of a specific protein or polypeptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequence. It should be further understood that the sequence includes the degenerate codons of the native sequence or sequences which may be introduced to provide codon preference in a specific host cell.

Substantial homology in the nucleic acid context means that the segments, or their complementary strands, when compared, are the same when properly aligned, with the appropriate nucleotide insertions or deletions, in at least about 60% of the nucleotides, typically, at least about 70%, more typically, at least about 80%, usually, at least about 90%, and more usually, at least about 95% to 98% of the nucleotides. Alternatively, substantial homology exists when the segments hybridize under selective hybridization conditions to a strand, or its complement, typically using a sequence of at least about 20 contiguous nucleotides derived from the nucleotide sequence shown in FIGS. 1A–1C (SEQ ID NO:7). However, larger segments will usually be preferred, e.g., at least about 30 contiguous nucleotides, more usually about 40 contiguous nucleotides, and preferably more than about 50 contiguous nucleotides. Selective hybridization exists when hybridization occurs which is more selective than that seen for nucleic acids displaying nonspecific interactions, i.e., are wholly unrelated. See, Kanehisa, Nucleic Acid Res. 12:203–213 (1984). Examples of such selective hybridization conditions include, e.g., hybridization under the hybridization and wash conditions of 50% formamide at 42° C. Other stringent hybridization conditions may also be selected. Generally, stringent conditions are selected to be about 50° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

There are various methods of isolating the nucleic acids which encode the polypeptides of the present invention.

Typically, the DNA is isolated from a genomic or cDNA library using labeled oligonucleotide probes specific for sequences in the desired DNA. Restriction endonuclease digestion of genomic DNA or cDNA containing the appropriate genes can be used to isolate the DNA encoding the polypeptides of the invention. From the nucleotide sequence given in FIGS. 1A–1C (SEQ ID NO:7), a panel of restriction endonucleases can be constructed to give cleavage of the DNA in desired regions, i.e., to obtain segments which encode biologically active fragments of the polypeptides of the invention. Following restriction endonuclease digestion, DNA encoding the polypeptides of the invention is identified by its ability to hybridize with a nucleic acid probe in, for example, a Southern blot format. These regions are then isolated using standard methods. See, e.g., Sambrook, et al., supra.

The polymerase chain reaction, or "PCR" can also be used to prepare nucleic acids which encode the polypeptides of the present invention. PCR technology is used to amplify nucleic acid sequences of the desired nucleic acid, e.g., the DNA which encodes the polypeptides of the invention, directly from mRNA, cDNA, or genomic or cDNA libraries. For example, DNA encoding full length FasL may be isolated from appropriate tissue libraries and PCR amplified, inserting a stop codon after the sequence encoding the extracellular domain, i.e., to delete the transmembrane domain, or as otherwise desired. Alternatively, solid phase oligonucleotide synthesis methods may also be employed to produce the nucleic acids described herein. Such methods include the phosphoramidite method described by, e.g., Beaucage and Carruthers, Tetrahedron Lett. 22:1859–1862 (1981), or the triester method according to Matteucci, et al., J. Am. Chem. Soc., 103:3185 (1981). A double stranded fragment may then be obtained, if desired, by annealing the chemically synthesized single strands together under appropriate conditions or by synthesizing the complementary strand using DNA polymerase with an appropriate primer sequence.

Appropriate primers and probes for amplifying the nucleic acids described herein, may be generated from analysis of the nucleic acid sequences described herein, e.g., shown in FIGS. 1A–1C (SEQ ID NO:7). Briefly, oligonucleotide primers complementary to the two 3' borders of the DNA region to be amplified are synthesized. The PCR is then carried out using the two primers. See, e.g., PCR Protocols: A Guide to Methods and Applications (Innis, M., Gelfand, D., Sninsky, J. and White, T., eds.) Academic Press (1990). Primers can be selected to amplify a variety of different sized segments from the nucleic acid sequence.

The present invention also includes fragments of the above described nucleic acids. Such fragments will generally comprise a segment of from about 15 to about 150 nucleotides. These fragments can be useful as oligonucleotide probes in the methods of the present invention, or alternatively to encode the polypeptides or biologically active fragments of the present invention, described herein. Also provided are substantially similar nucleic acid sequences, allelic variations and natural or induced sequences of the above described nucleic acids. Also included are chemically modified and substituted nucleic acids, e.g., those which incorporate modified nucleotide bases or which incorporate a labelling group.

In addition to comprising a segment which encodes one or more of the above described polypeptides or biologically active fragments, the nucleic acids of the present invention may also comprise a segment encoding a heterologous protein, such that the gene is expressed to produce the two proteins as a fusion protein, as substantially described above, e.g., the oligomerization promoting sequences, secretion directing sequences, or affinity target sequences as described herein.

Typically, the nucleic acids of the present invention will be used in expression vectors for the preparation of the polypeptides described above, i.e., in the production of cell lines that are capable of producing and preferably secreting the heterologous polypeptides of the invention. By "heterologous polypeptides" is meant a polypeptide that is not naturally produced and secreted by the particular host cell. The phrase "expression vector" generally refers to nucleotide sequences that are capable of affecting expression of a structural gene in hosts compatible with such sequences. These expression vectors typically include at least a suitable promoter sequence and optionally, transcription termination signals. Additional factors necessary or helpful in effecting expression may also be used as described herein. DNA encoding the polypeptides of the present invention will typically be incorporated into DNA constructs capable of introduction into and expression in an in vitro cell culture. Often, the nucleic acids of the present invention may be used to produce a suitable recombinant host cell. Specifically, DNA constructs will be suitable for replication in a cultured mammalian, plant, insect, yeast, fungi or other eukaryotic cell line. DNA constructs prepared for introduction into a particular host, e.g., mammalian or insect cell lines, will typically include a replication system recognized by the host, the intended DNA segment encoding the desired polypeptide, and transcriptional and translational initiation and termination regulatory sequences operably linked to the polypeptide encoding segment. A DNA segment is operably linked when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of the polypeptide. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof. The selection of an appropriate promoter sequence will generally depend upon the host cell selected for the expression of the DNA segment. Examples of suitable promoter sequences include prokaryotic, and eukaryotic promoters well known in the art. See, e.g., Sambrook et al., Molecular Cloning: A Laboratory Manual (2d ed.), vols. 1–3 Cold Spring Harbor Laboratory (1989). The transcriptional regulatory sequences will typically include a heterologous enhancer or promoter which is recognized by the host. The selection of an appropriate promoter will depend upon the host, and are generally well known and available. See Sambrook et al., (1989).

Conveniently available expression vectors which include the replication system and transcriptional and translational regulatory sequences together with the insertion site for the polypeptide encoding segment may be employed. Examples of workable combinations of cell lines and expression vectors are described in Sambrook et al., and in Metzger et al., Nature 334:31–36 (1988). For example, suitable expression vectors may be expressed in, e.g., COS-7 cells, by providing constructs for expression in mammalian cells, e.g., pCI-neo vector (available from Promega, Inc.). These constructs typically include the subject nucleic acids and employ an appropriate enhancer/promoter region. A wide variety of expression vectors suitable for such expression are commercially available from e.g., Promega, Invitrogen, Pharmingen, and the like. Alternatively, an insect cell line may be selected as the host cell of choice to express the polypeptide. In this case, the cDNA encoding the polypeptides of the invention may preferably be cloned into a baculovirus expression vector (e.g., pVL, pV-IKS, e.g. pVL1393 available from Pharmingen). The recombinant baculovirus may then be used to transfect a suitable insect host cell, e.g., Spodoptera frugiperda or "Sf9"cells, which may then express the polypeptide. See, e.g., D. K. Morrison et al., Cell 58:649–657 (1989), M. D. Summers and G. E. Smith, A Manual of Methods for Baculovirus Vectors and Insect Cell Culture Procedures, Texas Agricultural Station, College Station, Texas (1987). Baculoviral expression systems are preferred for their ability to produce large amounts of the expressed protein.

IV. Antibodies

The nucleic acids and polypeptides of the present invention or their immunologically active fragments are also useful in producing antibodies, either polyclonal or monoclonal, which are specifically immunoreactive with the polypeptides of the present invention.

The phrase "specifically immunoreactive," when referring to the interaction between an antibody of the invention and a particular polypeptide, refers to an antibody that specifically recognizes and binds with relatively high affinity to the particular protein, such that this binding is determinative of the presence of the protein in a heterogeneous population of proteins and other biologics. Thus, under designated immunoassay conditions, the specified antibodies bind to a particular protein and do not bind in a significant amount to other proteins present in the sample. A variety of immunoassay formats may be used to select antibodies specifically immunoreactive with a particular protein. For example, solid-phase ELISA immunoassays are routinely used to select monoclonal antibodies specifically immunoreactive with a protein. See, Harlow and Lane (1988) Antibodies, A Laboratory Manual, Cold Spring Harbor Publications, New York, for a description of immunoassay formats and conditions that can be used to determine specific immunoreactivity.

For production of polyclonal antibodies, an appropriate target immune system is selected, typically a mouse or rabbit, but also including goats, sheep, cows, guinea pigs, monkeys and rats. The substantially purified antigen or plasmid, e.g., a polypeptide or nucleic acid of the invention, is presented to the immune system in a fashion determined by methods appropriate for the animal. These and other parameters are well known to immunologists. Typically, injections are given in the footpads, intramuscularly, intradermally or intraperitoneally. The immunoglobulins produced by the host can be precipitated, isolated and purified by routine methods, including affinity purification.

For monoclonal antibodies, appropriate animals will be selected and the desired immunization protocol followed. After the appropriate period of time, the spleens of these animals are excised and individual spleen cells are fused, typically, to immortalized myeloma cells under appropriate selection conditions. Thereafter, the cells are clonally separated and the supernatants of each clone are tested for the production of an appropriate antibody specific for the desired region of the antigen. Techniques for producing antibodies are well known in the art. See, e.g., Goding et al., Monoclonal Antibodies: Principles and Practice (2d ed.) Acad. Press, N.Y., and Harlow and Lane, Antibodies: A Laboratory Manual, Cold Spring Harbor Laboratory, New York (1988). Other suitable techniques involve the in vitro exposure of lymphocytes to the antigenic polypeptides or alternatively, to selection of libraries of antibodies in phage or similar vectors. Huse et al., Generation of Large Combinatorial Library of the Immunoglobulin Repertoire in Phage Lambda, Science 246:1275–1281 (1989). Monoclonal antibodies with affinities of $10^8$ liters/mole, preferably $10^9$ to $10^{10}$ or stronger, will be produced by these methods.

The antibodies generated can be used for a number of purposes, including use as probes in immunoassays, inhibiting interaction between the Fas receptor and its ligands, e.g., endogenous FasL (thereby inhibiting or reducing Fas mediated mechanisms, e.g., apoptosis) in diagnostic or therapeutic applications, or in research to further elucidate the mechanism of Fas mediated pathways. Where the antibodies are used to block the interaction between two compounds or proteins, e.g., the Fas receptor and FasL, the antibody will generally be referred to as a "blocking antibody." Such blocking antibodies will generally be characterized by their relative ability to inhibit these interactions. Typically, a blocking antibody will have inhibitory activity as measured by an $IC_{50}$ of less than about 10 mM.

The antibodies of the present invention can be used with or without modification. Frequently, the antibodies will be labeled by joining, either covalently or non-covalently, a substance which provides for a detectable signal. Such labels include those that are well known in the art, such as the labels described previously for the polypeptides of the invention. Additionally, the antibodies of the invention may be chimeric, human-like or humanized, in order to reduce their potential antigenicity, without reducing their affinity for their target. Chimeric, human-like and humanized antibodies have generally been described in the art. Generally, such chimeric, human-like or humanized antibodies comprise hypervariable regions, e.g., complementarity determining regions (CDRs) from a mammalian animal, i.e., a mouse, and a human framework region. See, e.g., Queen, et al., Proc. Nat'l Acad. Sci. USA 86:10029 (1989), Verhoeyan, et al., Science 239:1534–1536 (1988). By incorporating as little foreign sequence as possible in the hybrid antibody, the antigenicity is reduced. Preparation of these hybrid antibodies may be carried out by methods well known in the art.

Preferred antibodies are those monoclonal or polyclonal antibodies which specifically recognize and bind the polypeptides of the invention. Accordingly, these preferred antibodies will specifically recognize and bind the polypeptides which have an amino acid sequence that is substantially homologous to the amino acid sequence shown in FIGS. 1A–1C (SEQ ID NO:8), or immunologically active fragments thereof. Still more preferred are antibodies which are capable of forming an antibody-ligand complex with the polypeptides of the invention, whereby the ability of the polypeptide to associate with its substrate or normally associated proteins, in vitro, is reduced, e.g., blocking antibodies.

V. Applications

The polypeptides, nucleic acids and cell lines of the present invention have a wide variety of uses, such as modelling and screening applications, therapeutic applications, and as affinity ligands for purifying or identifying compounds which are capable of specifically interacting with these compositions, e.g., Fas or related receptors, or cells expressing and presenting such receptors.

A. Modeling and Screening of Test Compounds

In a first application, the polypeptides of the invention may be used in in vitro or in vivo models to study the interaction between the Fas receptor and the Fas ligand (FasL), as well as the effects of that interaction on downstream events, e.g., Fas mediated apoptosis. Such models can be used to screen for and identify compounds that are capable of affecting that interaction, and can also be used for elucidating the mechanism of Fas mediated apoptosis, as well as irregularities in that mechanism, e.g., dysregulation.

The polypeptides of the present invention, in conjunction with a model Fas receptor, e.g., cells that express and or operate under the control of the Fas receptor, can be used as an in vitro model of Fas mediated biological mechanisms, e.g., to screen test compounds for the ability to affect the interaction between FasL and the Fas receptor, such as to function as inhibitors or enhancers of that interaction. By "a cell that operates under control of a Fas receptor" is meant a cell that includes a pathway or response that is regulated through activation or binding of a ligand to the Fas receptor. Typically, the model Fas receptor will provide a detectable result of the interaction between the Fas receptor and the FasL. Preferably, such detectable results include those results that occur naturally upon FasL/Fas receptor interaction, i.e., cell death. However, such detectable results may be engineered into the cell. Examples of engineered results include chimeric reporter systems wherein the cell surface receptor or a downstream signaling protein is provided fused to a heterologous signaling protein that is capable of producing a separate signal, whereby activation of the cell surface receptor activates the signal producing protein to produce a detectable signal. Such detectable signals may include, e.g., initiation of expression of an active enzyme which is readily detectable such as β-galactosidase, or alternatively, may result in the translocation of a detectable protein to the cell surface. Such reporter systems are known in the art.

"Test compounds" may be a chemical compound, a mixture of chemical compounds, a biological macromolecule, or an extract made from biological materials such as bacteria, plants, fungi, or animal cells or tissues. Typically, test compounds may include structural analogs or peptidomimetics which are derived from the polypeptides or antibodies described herein, and particularly their biologically active fragments, or ligands thereof. Test compounds are evaluated for potential activity as enhancers or inhibitors of Fas receptor/FasL interaction, by inclusion in screening assays described herein. An "enhancer" will result in an increase in the level of the particular observed activity, e.g., Fas mediated cell death, while an "inhibitor" will diminish the particular observed activity. The terms "enhancer" or "inhibitor" as used herein, do not imply any particular mechanism of function. Particularly targeted test compounds include polypeptide fragments of the polypeptides of the present invention and structural analogs, mimics or peptidomimetics of these peptides.

The screening methods of the present invention typically involve the incubation of a polypeptide, mimic or analogue of the present invention that is capable of initiating or activating Fas receptor mediated apoptosis, e.g., secFL, in the presence of a cell that is capable of such Fas mediated apoptosis. This incubation is typically carried out in the presence (test) and absence (control) of the particular test compound. Where the test compound is an inhibitor, it will generally produce a detectable result, e.g., a decrease in the level of cell death relative to a control. Conversely, where the test compound is an enhancer of that interaction, it will generally result in an increase in the level of cell death, or a decrease in viability, relative to the control.

Again, determination of relative cell death or viability may be determined by the well known methods described herein.

In a related embodiment, the present invention also provides kits for carrying out the above described screening methods. The kits of the present invention generally include a polypeptide of the present invention, e.g., secFL, or a biologically active fragment thereof, as well as a Fas receptor, or cells expressing and operating under the control of the Fas receptor. One or more of these components may generally be provided in premeasured aliquots. The aliquots can be contained in any suitable container such as a vial or a tube. The polypeptide component can be provided in solution or in lyophilized form and/or may be immobilized. The polypeptide preparation may also contain preservatives such as sodium azide or protease inhibitors such as EDTA. A carrier protein such as BSA or ovalbumin, usually between about 0.5–5%, may also be included to stabilize the polypeptide. The solution form of the polypeptide of the invention may contain up to 50% glycerol if the enzyme is to be stored frozen, e.g., at −20° C. to −70° C. If the polypeptide is provided in lyophilized form, the kit can include a reconstitution buffer to reconstitute the polypeptide, as well as a reaction buffer. Alternatively, the polypeptide can be added to the reaction buffer and the solution freeze dried. This form can be readily reconstituted in distilled water with the necessary salt components already present for the particular reaction to be screened, so that no additional reaction buffer need be supplied. Thus, depending on the form and composition of the polypeptide preparation, different buffers may be included in the kit and they may be provided in more than one aliquot. Although described in substantial detail herein, these buffers are generally optional. The appropriate substrate or ligand, depending upon the particular screening method used, may be provided in a similar fashion to that of the polypeptide component. The kits will also typically include additional reagents for carrying out the particular method, e.g., stains for detection, antibodies, solid supports and the like, as well as detailed operating instructions for their use. For example, where binding interactions are being screened, the receptor or ligand component will generally be supplied within the kit, already coupled to an appropriate solid support.

Once identified, particular inhibitors or enhancers may then be used to inhibit or enhance the activity of the polypeptides of the present invention. This may be particularly useful in therapeutic applications, as discussed in greater detail, below.

In a similar aspect, the compositions of the present invention may be used for in vivo modeling. Briefly, such in vivo models incorporate the same components as the in vitro models except that one component, typically the Fas-mediated biological mechanism (Fas-receptor and associated pathway), is supplied in the context of a living animal, e.g., a mouse or rat, which is capable of a Fas-mediated response, e.g., apoptosis of select tissue. Screening typically involves inoculation of the animal with a test compound. The animal is also administered a polypeptide of the invention. The polypeptide functions to artificially stimulate the Fas-mediated apoptotic pathway. The response of this pathway is measured and compared among inoculated and non-inoculated animals to determine whether the test compound inhibits or enhances the functioning of that pathway.

Measurement of this response is generally carried out by measurement or detection of a Fas mediated response. For example, as activation of the Fas receptor has been shown to cause death by fulminant liver damage, one may assess hepatic function in the animal. Alternatively, may determine the number of remaining or surviving Fas-responding cells, e.g., B and T cells, following inoculation. This is particularly important in those applications where the polypeptides of the invention are used as immunosuppressive agents, as described below.

B. Affinity Ligands

Because the compounds of the present invention are specifically reactive with the Fas receptor, they are particularly suited as affinity ligands for the identification and/or purification of such receptors, those receptors that are close structural and functional relatives of the Fas receptor, and cells that express on their surface the aforementioned receptors.

Typically, when using the polypeptides of the present invention as affinity ligands to purify Fas receptors or cells expressing such receptors, the polypeptides are incubated with a mixture of proteins, cells or the like, that contain a Fas receptor. For example, the polypeptides of the invention may be coupled to a suitable solid support and contacted with a mixture of proteins containing the Fas receptor component, e.g., as a free, soluble protein, or as a cell associated receptor, under conditions conducive to the association of the Fas receptor component with the immobilized polypeptide of the invention. Once bound to the immobilized polypeptide, the solid support is washed to remove unbound material and/or nonspecifically bound proteins. The desired receptors or cells may then be eluted from the solid support in substantially pure form by, e.g., a change in salt, pH or buffer concentration. Suitable solid supports for affinity purifications are well known in the art and are generally commercially available from, e.g., Pharmacia, Inc., or Sigma Chemical Co. Examples of such solid supports include agarose, cellulose, dextran, silica, polystyrene or similar solid supports.

Alternatively, when used for detection of the receptor components, the protein or cell mixtures suspected of containing these receptor components may be immobilized on a solid support, e.g., by blotting on a membrane such as nitrocellulose or PVDF, or coupled to the wells of a microwell plate. The immobilized mixture is then contacted with the polypeptide of the invention, and any receptor/ligand complex that is formed, is detected. As noted previously, in such applications, the polypeptide of the invention will typically be provided as a labeled compound, e.g., bearing a fluorescent, chemiluminescent, radioactive or enzymatic label. Following appropriate incubation and washing steps, detection of the formation of the complex then merely involves the detection of the label that remains attached to the solid support via its complexation with the bound receptor. The presence of the label is therefore indicative of the presence of the receptor component within the mixture. As will be appreciated, this method works equally well with heterogeneous mixtures of proteins or cells.

C. Therapeutic Use

In addition to the above described uses, the polypeptides, nucleic acids and antibodies of the present invention may also be used in therapeutic applications for the treatment of human or non-human mammalian patients. The term "treatment" or "treating a patient," as used herein, refers to the full spectrum of treatments for a given disorder from which the patient is suffering, including alleviation of one, most or all symptoms resulting from that disorder, outright cure for the particular disorder and prevention of the onset of the disorder. In the context of the present invention, such disorders typically are in some measure characterized by dysfunction of Fas-mediated pathways, and include those disorders characterized by either an inadequate or under-stimulation, e.g., persistence of auto-reactive B and T cells leading to lymphoproliferative disorders and acceleration of autoimmune disorders, or over-stimulation of these Fas-mediated pathways, resulting in premature cell death and fulminant liver damage.

By "under stimulation" is meant a level of Fas mediated activity that is below the level of Fas mediated activity normally occuring in vivo. Such under-stimulation may be characterized by the onset of one of the particular disorders described herein, or, alternatively, by the prevalence or persistence of Fas responding cells within the patient's system that is in excess of normal levels. Over-stimulation of Fas mediated activity may be conversely defined.

Treatment of those disorders that are characterized by an under-stimulation of the Fas mediated mechanisms typically involves administration to the patient of those polypeptides of the invention that are characterized by their ability to activate such Fas-mediated mechanisms or activity, e.g., secFL and its biologically active fragments. In this aspect, the polypeptides of the invention function as an exogenous source of soluble FasL, to regulate and stimulate a normal level of Fas-mediated activity. In a related aspect, the polypeptides of the present invention may also be administered to a patient as described herein, in order to augment the patient's normal level of Fas mediated activity, despite the fact that such activity does not result from an "under stimulation" per se. For example, over-activation of the Fas receptor may be desirable in a number of instances, such as in immunosuppression therapies, to reduce the populations of active lymphocytes. This is particularly useful in preventing graft rejection, and as described above, in treating autoimmune disorders. As will be appreciated, amounts for such therapy must be appropriately titrated to achieve desired results without causing excess tissue damage to the patient, i.e., resulting from systemic apoptotic cell death.

Generally, the above described treatments involve administering an effective amount of the polypeptides of the invention sufficient to augment the level of exogenous FasL in the patient's system to achieve normal or near normal Fas-mediated activity.

Treatment of those disorders characterized by an over-stimulation of these mechanisms typically involve administration to the patient of those compositions of the invention that are capable of blocking an interaction between the Fas receptor and a patient's endogenous Fas ligands, to inhibit or block the interaction of these compounds. For example, by administering to a patient an effective amount of an antibody to FasL, e.g., a blocking antibody, as described herein, one may block association of endogenous FasL with the Fas receptor and thereby reduce the level of Fas-mediated activation.

The quantities of reagents necessary for effective therapy, also referred to herein as an "effective amount," or "therapeutically effective amount," will depend upon many different factors, including means of administration, target site, physiological state of the patient and other medicants administered. Thus, treatment doses will need to be titrated to optimize safety and efficacy. Typically, dosages used in vitro may provide useful guidance in the amounts useful for in situ administration of these reagents. Animal testing of effective doses for treatment of particular disorders will provide further predictive indication of human dosage.

Generally, therapeutically effective amounts of the polypeptides of the present invention will be from about 0.0001 to about 10 mg/kg, and more usually, from about 0.001 to about 0.1 mg/kg of the host's body weight. Various considerations are described, e.g., in Gilman et al., (Eds.), Goodman and Gilman's: *The Pharmacological Basis of Therapeutics*, (8th ed. 1990), Pergamon Press, and *Remington's Pharmaceutical Sciences* (7th ed. 1985) Mack Publishing Co., Easton, Penn. Methods of administration, also discussed in the above references, include, e.g., oral, intravenous, intraperitoneal or intramuscular administration, and local administration, including topical, transdermal diffusion and aerosol administration, for therapeutic, and/or prophylactic treatment. The active agent, i.e., the polypeptide component, will generally be administered in a composition additionally comprising a pharmaceutically acceptable carrier. Suitable pharmaceutically acceptable carriers include water, saline, buffers and other compounds described in, e.g., the Merck Index, Merck and Co., Rahway, N.J. For some methods of administration, e.g., oral, it may be desirable to provide the active ingredient in a liposomal formulation. This is particularly desirable where the active ingredient may be subject to degradative environments, for example, proteolytic digestive enzymes. Liposomal formulations are well known in the art, and are discussed in, e.g., REMINGTON'S PHARMACEUICAL SCIENCES, supra. Administration may also be carried out by way of a controlled release composition or device, whereby a slow release of the active ingredient allows continuous administration over a longer period of time.

Constituents of pharmaceutical compositions, in addition to the active agents described herein, include those generally known in the art for the various administration methods used. For example, oral forms generally include powders, tablets, pills, capsules, lozenges and liquids. Similarly, intravenous, intraperitoneal or intramuscular formulations will generally be dissolved or suspended in a pharmaceutically acceptable carrier, e.g., water, buffered water, saline and the like. Additionally, these compositions may include additional constituents which may be required to approximate physiological conditions, such as pH adjusting and buffering agents, tonicity adjusting agents, wetting agents and the like. For solid compositions, conventional nontoxic solid carriers may be used which include, e.g., pharmaceutical grades of mannitol, lactose, starch, magnesium stearate, sodium saccharin, talcum, cellulose, glucose, sucrose, magnesium carbonate and the like.

Administration may also be carried out by way of a controlled release composition or device, whereby a slow release of the active ingredient allows continuous administration over a longer period of time.

The present invention is further illustrated by the following examples. These examples are merely to illustrate aspects of the present invention and are not intended as limitations of this invention.

VI. Examples

A. Cloning and Expression of SecFL

Full length human FasL was PCR amplified from spleen cDNA (Clontech, Quick-Clone) using ULTma DNA polymerase (Perkin-Elmer). The forward primer was (SEQ ID NO:1) 5'-TGCCATGCAGCAGCCCTTCAATTAC-3' (the initiating methionine codon is underlined) and the reverse primer was (SEQ ID NO:2) 5'-TTCTCTTAGAG CTTATATAAGCCG-3' (the stop codon is underlined). For the PCR, Ampliwax (Perkin-Elmer) was used for a hot start followed by 30 cycles of 95° C. (1 min), 50° C. (1 min), 72° C. (40 sec). The 853 bp CDNA was gel isolated and subcloned into pBluescript (Stratgene) by standard techniques. The entire extracellular domain of human CD8 was PCR amplified from pJN/CD8/R1 (provided by Dr. Blanche Shamoon). The forward primer was (SEQ ID NO:3) 5'-GCATGCGCTAGCATGGCCTTACCAGTGACC-3' (the initiating met codon is again underlined), and the reverse primer was (SEQ ID NO:4) 5'-GCCGAATTC GTGATGGTGATGGTGATGCTCGAGACAGG CGAAGTCCAG-3' (the six histidine residues are underlined). The extracellular domain of FasL was PCR amplified/mutagenized from the pBluescript/FasL vector. In secFL, the FasL protein sequence begins at amino acid residue 103 of the full length authentic or naturally occuring FasL protein. This is immediately proximal to the putative transmembrane region (See FIGS. 1A–1C). The forward primer was (SEQ ID NO:5) 5'-GCCGAATTC GAATACATGCCAATGGAACAGCTCTTC CACCTACAG-3' (the sequence encoding the glu-glu epitope tag is underlined). The reverse primer was (SEQ ID NO:4) 5'-CGCGGATCCTCTAGATTAGAGC TTATATAAGCC-3' (the stop codon is underlined). All DNA fragments were subcloned into pBluescript and sequences were confirmed on an ALF sequencer (Pharmacia). Fragments were assembled into pCI-neo (Promega) for expression in mammalian cells. Subsequently, the NheI-NotI fragment from pCIsecFL was subcloned into XbaI-NotI-digested pVL1393 (Pharmingen) to generate pVLsecFL.

Spodoptera frugiperda ("Sf9") cells were cotransfected with pVLsecFL and BaculoGold (Pharmingen). Extracellular virus particles were collected and amplified three times. For protein expression, Sf9 cells were infected at high density (>$10^8$ cells/150 $cm^2$) and incubated for four days in Sf900II media (Gibco BRL).

B. Purification of secreted secFL protein

Conditioned media from the FasL infected Sf9 cells was filtered through a 0.2 micron membrane, batch treated with 1/100th volume of ExtraciGelD beads (Pierce), and then precipitated with 80% (saturating) ammonium sulfate. Alternatively, secFL-conditioned media is dialyzed against phosphate-buffered saline plus glycerol and then purified by binding to TALON resin (Clontech).

C. Assaying Cell Death

To determine ability to stimulate cell death, two cultured cell lines were used to assess killing by Sf9-produced secFL; human jurkat T cells and stable lines of Rat2 cells transfected with the human Fas receptor. Cell death was easily monitored by visual inspection. In particular, human Jurkat T cells were treated for varying lengths of time to CH-11 anti-Fas IgM at 1 $\mu$g/ml (positive control) or with secFL. The secFL was prepared from COS6M cells transfected with pCIsecFL using DEAE-dextran and then incubating the cells for three days in OptiMEM containing 4% fetal bovine serum. The conditioned COS media was added at a 1:2 dilution to the Jurkat cells in the same media. FIG. 2 shows a comparison of cell death as a function of treatment time in the positive control (open squares) and the secFL treated cells (diamonds). Cell death was monitored by standard assay methods (DNA fragmentation ELISA, Boehringer Mannheim). The results shown in FIG. 2 confirm the efficacy of secFL in activating the cell death mechanism.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to

What is claimed is:

1. A polypeptide which binds to a Fas receptor, said polypeptide comprising an extracellular domain of CD8, a heterologous marker sequence, and an extracellular domain of Fas ligand (FasL), wherein said polypeptide is encoded by a nucleic acid sequence that selectively hybridizes to the complete complementary nucleic acid sequence shown in SEQ ID NO:7 or to the complete complimentary nucleic acid sequence shown in SEQ ID NO:7 in which one or more codons of SEQ ID NO: 7 have been substituted by a degenerate codon.

2. The polypeptide of claim 1, wherein said heterologous marker sequence comprises an antibody binding epitope.

3. The polypeptide of claim 1, wherein said heterologous marker sequence comprises a hexahistidine motif.

4. The polypeptide of claim 2, wherein said heterologous marker sequence is a glu-glu epitope tag.

5. The polypeptide of claim 1, wherein said polypeptide activates Fas mediated apoptosis.

6. The polypeptide of claim 1, wherein said polypeptide is encoded by a nucleic acid sequence that selectively hybridizes to the complete complementary nucleic acid sequence shown in SEQ ID NO:7.

7. The polypeptide of claim 1, said polypeptide comprising the amino acid sequence of SEQ ID NO:8.

8. A polypeptide which binds to a Fas receptor, wherein said polypeptide is encoded by the nucleic acid sequence shown in SEQ ID NO:7 or by the nucleic acid sequence shown in SEQ ID NO:7 in which one or more codons of SEQ ID NO: 7 have been substituted by a degenerate codon.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
           (A) LENGTH: 25 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:1:

TGCCATGCAG CAGCCCTTCA ATTAC                                             25

(2) INFORMATION FOR SEQ ID NO:2:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:2:

TTCTCTTAGA GCTTATATAA GCCG                                              24

(2) INFORMATION FOR SEQ ID NO:3:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:3:

GCATGCGCTA GCATGGCCTT ACCAGTGACC                                        30

(2) INFORMATION FOR SEQ ID NO:4:

(i) SEQUENCE CHARACTERISTICS:
           (A) LENGTH: 48 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:4:

GCCGAATTCG TGATGGTGAT GGTGATGCTC GAGACAGGCG AAGTCCAG                    48

(2) INFORMATION FOR SEQ ID NO:5:

(i) SEQUENCE CHARACTERISTICS:
           (A) LENGTH: 45 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:5:

GCCGAATTCG AATACATGCC AATGGAACAG CTCTTCCACC TACAG                45

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CGCGGATCCT CTAGATTAGA GCTTATATAA GCC                             33

(2) INFORMATION FOR SEQ ID NO:7:

(i) SEQUENCE CHARACTERISTICS:
        (A) LENGTH: 1131 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1128

(xi) SEQUENCE DESCRIPTION: SEQ ID NO:7:

```
ATG GCC TTA CCA GTG ACC GCC TTG CTC CTG CCG CTG GCC TTG CTG CTC    48
Met Ala Leu Pro Val Thr Ala Leu Leu Leu Pro Leu Ala Leu Leu Leu
 1               5                  10                  15

CAC GCC GCC AGG CCG AGC CAG TTC CGG GTG TCG CCG CTG GAT CGG ACC    96
His Ala Ala Arg Pro Ser Gln Phe Arg Val Ser Pro Leu Asp Arg Thr
                20                  25                  30

TGG AAC CTG GGC GAG ACA GTG GAG CTG AAG TGC CAG GTG CTG CTG TCC   144
Trp Asn Leu Gly Glu Thr Val Glu Leu Lys Cys Gln Val Leu Leu Ser
            35                  40                  45

AAC CCG ACG TCG GGC TGC TCG TGG CTC TTC CAG CCG CGC GGC GCC GCC   192
Asn Pro Thr Ser Gly Cys Ser Trp Leu Phe Gln Pro Arg Gly Ala Ala
        50                  55                  60

GCC AGT CCC ACC TTC CTC CTA TAC CTC TCC CAA AAC AAG CCC AAG GCG   240
Ala Ser Pro Thr Phe Leu Leu Tyr Leu Ser Gln Asn Lys Pro Lys Ala
65                  70                  75                  80

GCC GAG GGG CTG GAC ACC CAG CGG TTC TCG GGC AAG AGG TTG GGG GAC   288
Ala Glu Gly Leu Asp Thr Gln Arg Phe Ser Gly Lys Arg Leu Gly Asp
                85                  90                  95

ACC TTC GTC CTC ACC CTG AGC GAC TTC CGC CGA GAG AAC GAG GGC TAC   336
Thr Phe Val Leu Thr Leu Ser Asp Phe Arg Arg Glu Asn Glu Gly Tyr
                100                 105                 110

TAT TTC TGC TCG GCC CTG AGC AAC TCC ATC ATG TAC TTC AGC CAC TTC   384
Tyr Phe Cys Ser Ala Leu Ser Asn Ser Ile Met Tyr Phe Ser His Phe
            115                 120                 125

GTG CCG GTC TTC CTG CCA GCG AAG CCC ACC ACG ACG CCA GCG CCG CGA   432
Val Pro Val Phe Leu Pro Ala Lys Pro Thr Thr Thr Pro Ala Pro Arg
        130                 135                 140

CCA CCA ACA CCG GCG CCC ACC ATC GCG TCG CAG CCC CTG TCC CTG CGC   480
Pro Pro Thr Pro Ala Pro Thr Ile Ala Ser Gln Pro Leu Ser Leu Arg
145                 150                 155                 160

CCA GAG GCG TGC CGG CCA GCG GCG GGG GGC GCA GTG CAC ACG AGG GGG   528
Pro Glu Ala Cys Arg Pro Ala Ala Gly Gly Ala Val His Thr Arg Gly
                165                 170                 175
```

```
CTG GAC TTC GCC TGT CTC GAG CAT CAC CAT CAC CAT CAC GAA TTC GAA        576
Leu Asp Phe Ala Cys Leu Glu His His His His His His Glu Phe Glu
        180                 185                 190

TAC ATG CCA ATG GAA CAG CTC TTC CAC CTA CAG AAG GAG CTG GCA GAA        624
Tyr Met Pro Met Glu Gln Leu Phe His Leu Gln Lys Glu Leu Ala Glu
            195                 200                 205

CTC CGA GAG TCT ACC AGC CAG ATG CAC ACA GCA TCA TCT TTG GAG AAG        672
Leu Arg Glu Ser Thr Ser Gln Met His Thr Ala Ser Ser Leu Glu Lys
    210                 215                 220

CAA ATA GGC CAC CCC AGT CCA CCC CCT GAA AAA AAG GAG CTG AGG AAA        720
Gln Ile Gly His Pro Ser Pro Pro Pro Glu Lys Lys Glu Leu Arg Lys
225                 230                 235                 240

GTG GCC CAT TTA ACA GGC AAG TCC AAC TCA AGG TCC ATG CCT CTG GAA        768
Val Ala His Leu Thr Gly Lys Ser Asn Ser Arg Ser Met Pro Leu Glu
                245                 250                 255

TGG GAA GAC ACC TAT GGA ATT GTC CTG CTT TCT GGA GTG AAG TAT AAG        816
Trp Glu Asp Thr Tyr Gly Ile Val Leu Leu Ser Gly Val Lys Tyr Lys
            260                 265                 270

AAG GGT GGC CTT GTG ATC AAT GAA ACT GGG CTG TAC TTT GTA TAT TCC        864
Lys Gly Gly Leu Val Ile Asn Glu Thr Gly Leu Tyr Phe Val Tyr Ser
    275                 280                 285

AAA GTA TAC TTC CGG GGT CAA TCT TGC AAC AAC CTG CCC CTG AGC CAC        912
Lys Val Tyr Phe Arg Gly Gln Ser Cys Asn Asn Leu Pro Leu Ser His
290                 295                 300

AAG GTC TAC ATG AGG AAC TCT AAG TAT CCC CAG GAT CTG GTG ATG ATG        960
Lys Val Tyr Met Arg Asn Ser Lys Tyr Pro Gln Asp Leu Val Met Met
305                 310                 315                 320

GAG GGG AAG ATG ATG AGC TAC TGC ACT ACT GGG CAG ATG TGG GCC CGC       1008
Glu Gly Lys Met Met Ser Tyr Cys Thr Thr Gly Gln Met Trp Ala Arg
                325                 330                 335

AGC AGC TAC CTG GGG GCA GTG TTC AAT CTT ACC AGT GCT GAT CAT TTA       1056
Ser Ser Tyr Leu Gly Ala Val Phe Asn Leu Thr Ser Ala Asp His Leu
            340                 345                 350

TAT GTC AAC GTA TCT GAG CTC TGT CTG GTC AAT TTT GAG GAA TCT CAG       1104
Tyr Val Asn Val Ser Glu Leu Cys Leu Val Asn Phe Glu Glu Ser Gln
    355                 360                 365

ACG TTT TTC GGC TTA TAT AAG CTC TAA                                   1131
Thr Phe Phe Gly Leu Tyr Lys Leu
370                 375

(2) INFORMATION FOR SEQ ID NO:8:

(i) SEQUENCE CHARACTERISTICS:
        (A) LENGTH: 376 amino acids
        (B) TYPE: amino acid
        (D) TOPOLOGY: linear (ii) MOLECULE TYPE: protein (xi) SEQUENCE DESCRIPTION: SEQ ID NO:8:

Met Ala Leu Pro Val Thr Ala Leu Leu Leu Pro Leu Ala Leu Leu Leu
 1               5                  10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
        50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
```

-continued

```
                  85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160
Pro Glu Ala Cys Arg Pro Ala Ala Gly Gly Ala Val His Thr Arg Gly
                165                 170                 175
Leu Asp Phe Ala Cys Leu Glu His His His His His His Glu Phe Glu
            180                 185                 190

Tyr Met Pro Met Glu Gln Leu Phe His Leu Gln Lys Glu Leu Ala Glu
        195                 200                 205

Leu Arg Glu Ser Thr Ser Gln Met His Thr Ala Ser Ser Leu Glu Lys
    210                 215                 220

Gln Ile Gly His Pro Ser Pro Pro Pro Glu Lys Lys Glu Leu Arg Lys
225                 230                 235                 240
Val Ala His Leu Thr Gly Lys Ser Asn Ser Arg Ser Met Pro Leu Glu
                245                 250                 255
Trp Glu Asp Thr Tyr Gly Ile Val Leu Leu Ser Gly Val Lys Tyr Lys
            260                 265                 270

Lys Gly Gly Leu Val Ile Asn Glu Thr Gly Leu Tyr Phe Val Tyr Ser
        275                 280                 285

Lys Val Tyr Phe Arg Gly Gln Ser Cys Asn Asn Leu Pro Leu Ser His
    290                 295                 300

Lys Val Tyr Met Arg Asn Ser Lys Tyr Pro Gln Asp Leu Val Met Met
305                 310                 315                 320
Glu Gly Lys Met Met Ser Tyr Cys Thr Thr Gly Gln Met Trp Ala Arg
                325                 330                 335
Ser Ser Tyr Leu Gly Ala Val Phe Asn Leu Thr Ser Ala Asp His Leu
            340                 345                 350
Tyr Val Asn Val Ser Glu Leu Cys Leu Val Asn Phe Glu Glu Ser Gln
        355                 360                 365

Thr Phe Phe Gly Leu Tyr Lys Leu
    370                 375
```